(12) United States Patent
Prstojevich

(10) Patent No.: US 8,337,212 B2
(45) Date of Patent: *Dec. 25, 2012

(54) MULTI-MODE ACCELERATION-BASED ATHLETICISM MEASUREMENT SYSTEM

(75) Inventor: Michael Prstojevich, Portland, OR (US)

(73) Assignee: Nike, Inc., Beaverton, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/358,166

(22) Filed: Jan. 25, 2012

(65) Prior Publication Data

US 2012/0123569 A1    May 17, 2012

Related U.S. Application Data

(63) Continuation of application No. 11/864,438, filed on Sep. 28, 2007, now Pat. No. 8,128,410.

(60) Provisional application No. 60/848,271, filed on Sep. 29, 2006.

(51) Int. Cl.
    *A63B 69/00* (2006.01)

(52) U.S. Cl. .............................. 434/247; 434/255; 482/3

(58) Field of Classification Search .................. 434/265, 434/247
    See application file for complete search history.

(56) References Cited

U.S. PATENT DOCUMENTS

| 1,020,005 | A | * | 3/1912 | Witthoefft | 249/186 |
|---|---|---|---|---|---|
| 3,492,582 | A | * | 1/1970 | Heywood | 340/323 R |
| 3,797,010 | A | * | 3/1974 | Adler et al. | 340/323 R |
| 4,978,303 | A | * | 12/1990 | Lampbell | 434/258 |
| 5,149,084 | A | * | 9/1992 | Dalebout et al. | 482/3 |
| 5,300,921 | A | * | 4/1994 | Hoch et al. | 340/573.6 |
| 5,524,637 | A | * | 6/1996 | Erickson | 600/592 |
| 5,613,924 | A | * | 3/1997 | Lee | 482/51 |
| 5,737,280 | A | * | 4/1998 | Kokubo | 368/2 |
| 5,916,063 | A | * | 6/1999 | Alessandri | 482/4 |
| 5,937,387 | A | * | 8/1999 | Summerell et al. | 705/2 |
| 5,944,633 | A | * | 8/1999 | Wittrock | 482/4 |
| 5,976,083 | A | * | 11/1999 | Richardson et al. | 600/300 |
| 6,013,007 | A | * | 1/2000 | Root et al. | 482/8 |
| 6,132,337 | A | * | 10/2000 | Krupka et al. | 482/8 |
| 6,231,481 | B1 | * | 5/2001 | Brock | 482/8 |
| 6,292,792 | B1 | * | 9/2001 | Baffes et al. | 706/45 |
| 6,356,856 | B1 | * | 3/2002 | Damen et al. | 702/160 |
| 6,449,583 | B1 | * | 9/2002 | Sakumoto et al. | 702/179 |
| 6,450,922 | B1 | * | 9/2002 | Henderson et al. | 482/8 |
| 6,458,060 | B1 | * | 10/2002 | Watterson et al. | 482/54 |
| 6,493,652 | B1 | * | 12/2002 | Ohlenbusch et al. | 702/160 |
| 6,513,381 | B2 | * | 2/2003 | Fyfe et al. | 73/510 |
| 6,585,622 | B1 | * | 7/2003 | Shum et al. | 482/8 |
| 6,605,038 | B1 | * | 8/2003 | Teller et al. | 600/300 |

(Continued)

FOREIGN PATENT DOCUMENTS

WO    2006053000    5/2006

*Primary Examiner* — Robert J Utama
(74) *Attorney, Agent, or Firm* — Banner & Witcoff, Ltd.

(57) ABSTRACT

A multi-mode athleticism movement measurement system includes an athlete-borne acceleration sensor and an athleticism processing device to determine athleticism information based upon one or more timing measurements from the athlete-borne acceleration sensor, the athleticism information corresponding to any of multiple athleticism measurement modes available on athleticism processing device and selectable by a user. A data link between the athlete-borne acceleration sensor and the athleticism rating processing device transmits the one or more timing measurements from the athlete-borne acceleration sensor to the athleticism rating processing device.

18 Claims, 5 Drawing Sheets

U.S. PATENT DOCUMENTS

| | | | |
|---|---|---|---|
| 6,736,759 B1 * | 5/2004 | Stubbs et al. | 482/8 |
| 6,825,875 B1 * | 11/2004 | Strub et al. | 348/207.99 |
| 6,837,827 B1 * | 1/2005 | Lee et al. | 482/8 |
| 6,876,947 B1 | 4/2005 | Darley et al. | |
| 6,882,955 B1 | 4/2005 | Ohlenbusch et al. | |
| 6,898,550 B1 | 5/2005 | Blackadar et al. | |
| 7,056,265 B1 * | 6/2006 | Shea | 482/8 |
| 7,072,789 B2 * | 7/2006 | Vock et al. | 702/141 |
| 7,081,809 B1 * | 7/2006 | Mix et al. | 340/321 |
| 7,192,387 B2 * | 3/2007 | Mendel | 482/8 |
| 7,220,220 B2 * | 5/2007 | Stubbs et al. | 482/72 |
| 7,278,966 B2 | 10/2007 | Hjelt et al. | |
| 7,398,151 B1 * | 7/2008 | Burrell et al. | 701/410 |
| 7,503,878 B1 * | 3/2009 | Amsbury et al. | 482/9 |
| 7,519,327 B2 * | 4/2009 | White | 455/41.2 |
| 7,534,206 B1 * | 5/2009 | Lovitt et al. | 600/300 |
| 7,603,255 B2 * | 10/2009 | Case et al. | 702/182 |
| 7,824,309 B1 * | 11/2010 | Tadlock | 482/3 |
| 2001/0041647 A1 * | 11/2001 | Itoh et al. | 482/9 |
| 2002/0019296 A1 * | 2/2002 | Freeman et al. | 482/4 |
| 2002/0055857 A1 * | 5/2002 | Mault | 705/2 |
| 2002/0091796 A1 * | 7/2002 | Higginson et al. | 709/218 |
| 2002/0116147 A1 * | 8/2002 | Vock et al. | 702/182 |
| 2003/0163283 A1 * | 8/2003 | O'Brien | 702/160 |
| 2005/0107216 A1 * | 5/2005 | Lee et al. | 482/8 |
| 2005/0202934 A1 * | 9/2005 | Olrik et al. | 482/8 |
| 2006/0063980 A1 * | 3/2006 | Hwang et al. | 600/300 |
| 2007/0272011 A1 * | 11/2007 | Chapa et al. | 73/379.01 |
| 2008/0090703 A1 * | 4/2008 | Rosenberg | 482/8 |
| 2008/0188354 A1 * | 8/2008 | Pauws et al. | 482/8 |
| 2008/0280730 A1 * | 11/2008 | Alexanderson | 482/9 |

* cited by examiner

MULTI-MODE ACCELERATION-BASED ATHLETICISM MEASUREMENT SYSTEM

RELATED APPLICATION

This application is a continuation of and claims the benefit of priority from co-pending U.S. non-provisional application Ser. No. 11/864,438 filed Sep. 28, 2007, and U.S. provisional application No. 60/848,271, filed Sep. 29, 2006, both of which are hereby incorporated by reference.

BACKGROUND AND SUMMARY OF THE INVENTION

Speed, agility, reaction time, and power are some of the determining characteristics influencing the athleticism of an athlete. Athletes strive to improve their athletic performance in these areas, and coaches and recruiters tend to seek those athletes that have the best set of these characteristics for the particular sport.

One method for evaluating and comparing athletes' athleticism involves having the athletes perform a common set of exercises and drills. Athletes that perform the exercises or drills more quickly or more accurately are usually considered to be better than those with slower or less accurate performance for the same exercise or drill. For example, "cone drills" are routinely used in training and evaluating athletes. In a typical "cone drill" the athlete must follow a pre-determined course between several marker cones and, in the process, execute a number of rapid direction changes, and/or switch from forward to backward or lateral running.

Prior systems have utilized accelerometers in or on footwear to discern footsteps or foot strikes of a runner (or walker) and have calculated corresponding running (walking) speed and distance. Examples of such systems are described in U.S. Pat. Nos. 6,513,381, 6,876,947; 6,882,955; 6,898,550, and 7,072,789. However, such accelerometer systems have not been utilized to measure the particular metrics that form the basis of determining broader athleticism ratings.

The present invention includes an athleticism movement measurement system having an athlete-borne movement sensor, such as an accelerometer (e.g., piezoelectric accelerometer), which is borne by an athlete. The athlete-borne acceleration sensor determines timing data for selected athletic drills, and the timing data are delivered to an athleticism rating processing device to determine an athleticism rating based upon the timing data. In one implementation, the timing data are delivered from the sensor to the processing device over a wireless data link.

Additional objects and advantages of the present invention will be apparent from the detailed description of the preferred embodiment thereof, which proceeds with reference to the accompanying drawings.

DETAILED DESCRIPTION OF THE INVENTION

Figure 1:
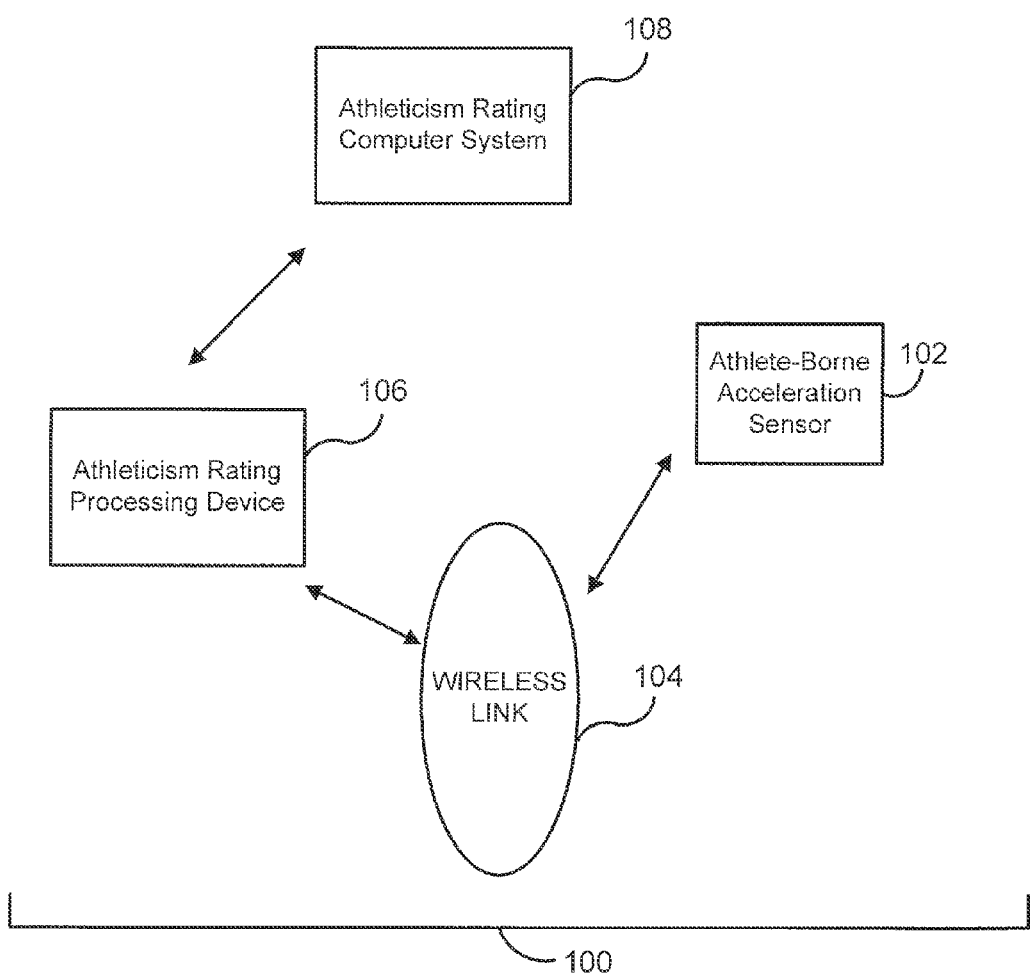
FIG. 1 is a block diagram of an athleticism movement measurement system.

FIG. 1 is a block diagram of a multi-mode acceleration-based athleticism measurement system 100 that includes a movement sensor 102 (e.g., an accelerometer, compression sensor, inertial measurement system, etc.) that is borne by an athlete during different athletic drills or tests to generate acceleration data that are used to generate an athleticism rating, such as a rating described in International patent application no. PCT/US2005/040493 for Athleticism Rating and Performance Measuring Systems, filed by SPARQ, Inc. and incorporated herein by reference. Sensor 12 may include any movement sensor (such as a piezoelectric sensor) that produces voltage or current proportional to acceleration, mechanical stress or strain, etc. For example, a piezoelectric sensor is a highly reliable vibration sensor, accelerometer and dynamic switch element that can detect foot strikes over time to measure athletic performance.

Acceleration sensor 102 may be positioned in a shoe, on top of a shoe, fastened around the ankle or wrist, attached to waist belts or incorporated into apparel on the body of the athlete, or otherwise borne by the athlete. In embodiments described below, an acceleration sensor 102 is positioned in or secured to one or each of an athlete's shoes.

Acceleration sensor 102 communicates over a link 104 with an athleticism rating processing device 106. In one implementation link 104 is a wireless, digital, low-power RF link with 1- or 2-way transmission, but a wired link could alternatively be employed in some applications. Athleticism rating processing device 106 may include one or more of an athleticism timing system, such as a SPARQ XLR8 Digital Timing system, available from SPARQ Marketing & Media of Portland, Oreg., or a stopwatch, sport watch, digital music player (e.g., iPod® media player), cell phone, wireless athleticism measurement kiosk, etc. configured to communicate over link 104 with acceleration sensor 102.

Athleticism rating processing device 106 allows a user (e.g., an athlete, coach, etc.) to select an athleticism measurement mode from among multiple selectable athleticism measurement modes. During a measurement mode, athleticism rating processing device 106 obtains and stores acceleration data from acceleration sensor 102 and selected timing data. In addition, athleticism rating processing device 106 may cue the athlete to perform certain actions during an athleticism measurement or may provide feedback during or after the measurement.

In one implementation, athleticism rating processing device 106 delivers the acceleration data and the timing data by wired or wireless communication to an athleticism rating computer system 108 that calculates an athleticism rating based in part on the acceleration data and timing data. Athleticism rating computer system 108 can be at the location where the athlete performs the athletic drills or tests or may be accessed over a computer network (e.g., the Internet). In an alternative implementation, athleticism rating processing device 106 may calculate an athleticism rating directly.

Figure 2:
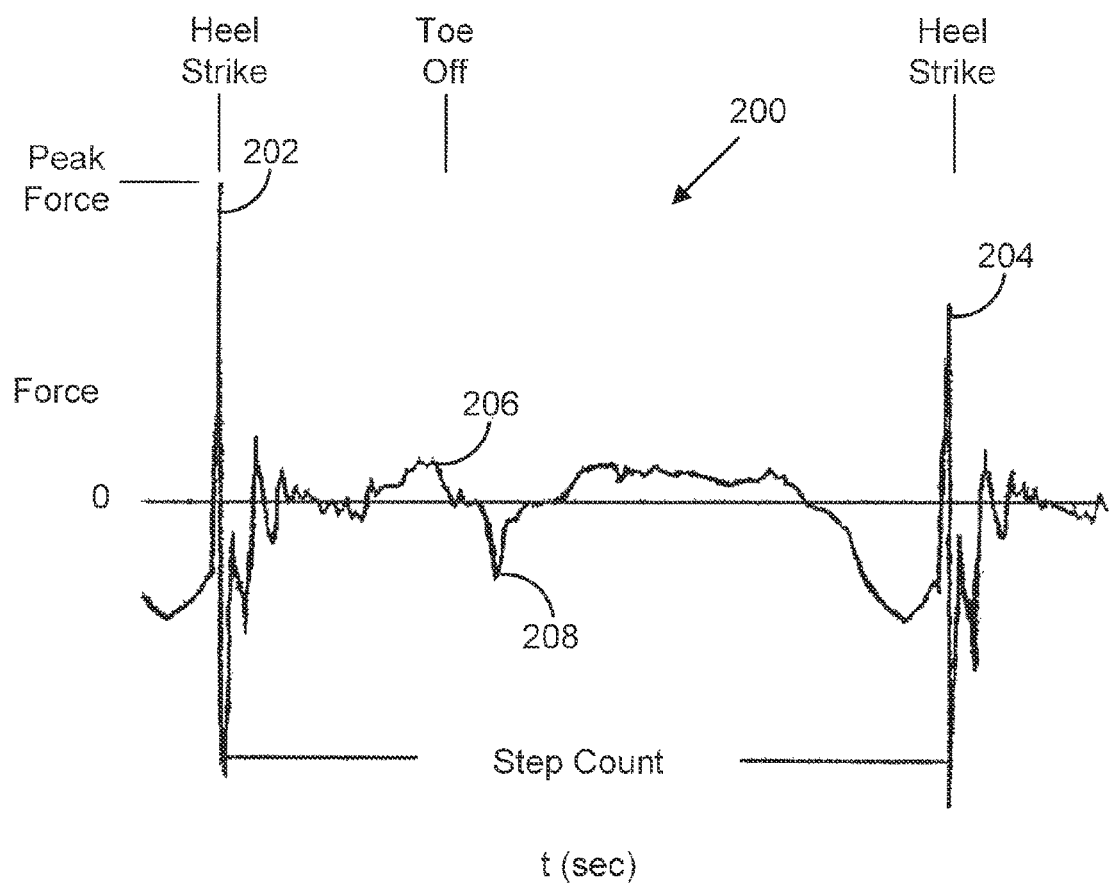
FIG. 2 is a prior art graph of acceleration readings from a shoe-mounted one-dimensional accelerometer during a running stride.

FIG. 2 is graph 200 of prior art acceleration readings from a vertical, one-dimensional shoe-mounted accelerometer during the time period of a running stride to illustrate characteristics of acceleration readings during an athletic activity. Graph 200 includes a first major positive acceleration spike 202 corresponding to a heel strike during a running stride and a second major positive acceleration spike 204 corresponding to a subsequent strike during the running stride. A prolonged secondary positive acceleration peak 206 preceding a negative acceleration spike 208 corresponds to a "toe-off" phase of the running stride.

Prior art acceleration readings form the basis of determining a running or walking speed, as described in U.S. Pat. No. 6,513,381 of Dynastream Innovations, Inc. In contrast, multi-mode acceleration-based athleticism measurement system 100 employs acceleration readings such as that represented by graph 200 in multiple different modes to measure performance in multiple different athletic tests or drills.

As described in International Patent Application No. PCT/US2005/040493, International Publication No. WO 2006/053000 for Athleticism Rating and Performance Measuring Systems, athleticism ratings are calculated from performance results of multiple athletic tests or drills. Multi-mode acceleration-based athleticism measurement system 100 generates acceleration and timing data in multiple distinct modes that correspond to different athletic tests or drills for use in determining an athleticism rating or improving performance in the different tests or drills. Each mode is selectable by an athlete or other user at athleticism rating processing device 106.

For example, multi-mode acceleration-based athleticism measurement system 100 can also be used in drills or tests that characterize agility or "fast feet" by calculating foot contact time or time aloft, such as in ladder and hurdle training drills in which minimization of foot contact time compared to elapsed time is desirable. Foot contact time refers to the time an athlete's foot is in contact with the ground surface, and loft time refers to the time between successive foot contact times during which the athlete's foot is raised above the ground surface. It will be appreciated that "ground surface" refers to any surface or surfaces on which an athlete might act, including athletic fields or tracks or floors, or any other surfaces whether or not specially adapted or designated for athletic performance.

Figure 3:
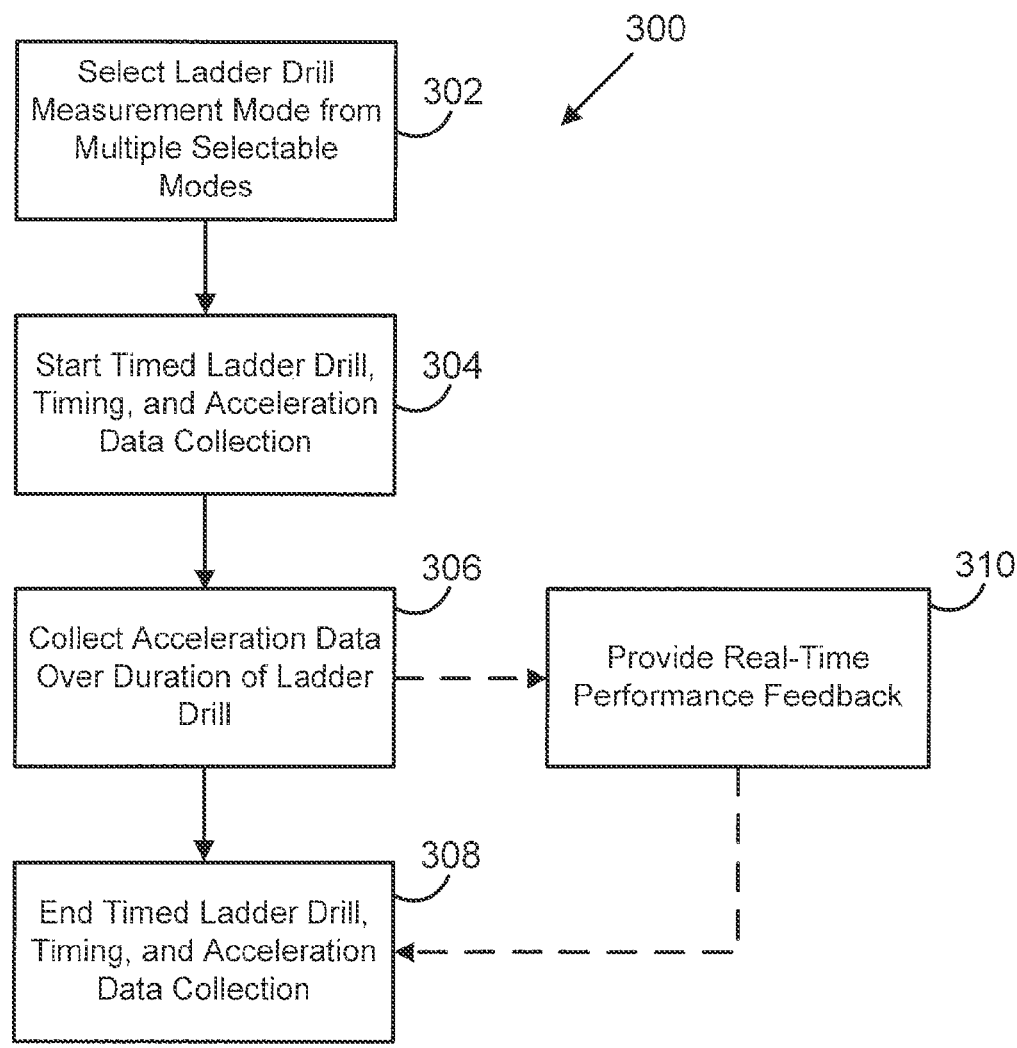
FIG. 3 is a flow diagram of an agility athletic performance measurement method as an illustration of one athleticism measurement mode according to the present invention.

FIG. 3 is a flow diagram of an agility athletic performance measurement method 300 that may be performed during a ladder/hurdle drill may be used in connection with calculating an athletic performance rating or in improving performance in the drill. In a ladder drill, an athlete side steps as quickly as possible into and out of multiple successive regions analogous to spaces between the rungs of a ladder laying flat on the ground. In a hurdle drill, the athlete side moves as quickly as possible over successive hurdles. Conventionally, performance in both types of drill is measured by the overall time in which the athlete completes the drill. Agility athletic performance measurement method 300 may employ an acceleration sensor 102 positioned in or secured to one or each of the athlete's shoes, preferably an acceleration sensor 102 being positioned in or secured to each of the athlete's shoes. The following description refers to a ladder/hurdle drill to indicate the applicability of method 300 to either drill or the like.

In step 302 a ladder/hurdle drill is selected from among multiple selectable drills or exercises, which correspond to different measurement modes, listed on athleticism rating processing device 106 that is worn or carried by the athlete.

In step 304 a timed ladder/hurdle drill is started together with a start of timing of the overall drill duration and a start of collecting of acceleration data by athleticism measurement system 100 in a ladder/hurdle drill mode. The acceleration data may be collected by athleticism rating processing device 106 that is worn, carried, or otherwise borne by the athlete. The start of timing of the overall drill duration may be initiated manually by an observer activating a timer or by the athlete crossing an optical timing start beam, and the start of collecting of acceleration data may be initiated by transmission of a wireless control signal to athleticism rating processing device 106 upon initiation of the overall timing.

In step 306 acceleration data are collected by athleticism measurement system 100 over the duration of the ladder/hurdle drill.

In step 308 the timed ladder/hurdle drill is ended together with timing of the overall drill duration and the collecting of acceleration data by athleticism measurement system 100. The timing of the overall drill duration may be ended manually by an observer de-activating a timer or by the athlete crossing an optical timing end beam, and the collecting of acceleration data may be ended by transmission of a wireless control signal to athleticism rating processing device 106 upon ending of the overall timing.

With an acceleration sensor 102 being positioned in or secured to each of the athlete's shoes, the acceleration data can indicate a ladder/hurdle step frequency or duration for each step in the drill, including distinguishing between the time each foot is on the ground surface and not on the ground surface. A drilling and testing goal of the ladder/hurdle drill is for an athlete to minimize the time each foot spends on the ground at each step (i.e., "fast feet"). The acceleration data, as an indicator of the ground contact time for each foot during the ladder/hurdle drill, can be applied as a factor in an athleticism rating or as a guide to assist an athlete in improving ladder/hurdle drill skills. Likewise, such acceleration data can identify asymmetry in the ground contact time for the athlete's right and left feet. This asymmetry data can also be applied as a factor in an athleticism rating or as a guide to assist an athlete in improving the athlete's strength, speed and agility drill skills.

Step 310 is an optional additional step in method 300 and occurs during collection of the acceleration data. Step 310 indicates that the athlete is given real-time feedback as to whether the drill performance meets a predetermined performance criterion, such as whether the athlete's foot contact time is less than a predefined threshold foot contact time to satisfy a "fast feet" criterion. In one implementation, the predefined threshold foot contact time can be set or selected at athleticism rating processing device 106 (e.g., 0.25 sec). The real-time feedback can be audible or visual feedback provided by athleticism rating processing device 106 during the drill indicating whether the athlete's performance meets or fails to meet the threshold.

For example, an audible indicator could employ one tone to indicate that the criterion is being met, while a different tone indicates that the criterion is not being met. Likewise, a visual indicator could employ one color (e.g., green) to indicate that the criterion is being met, while a different color (e.g., red) indicates that the criterion is not being met. Such instantaneous and continuous feedback allows an athlete to modify performance during the drill. A coach could such feedback to test athlete performance in real time and also to set training goals for an athlete.

In addition, an average contact time for each foot can be calculated to determine whether one foot/leg is slower than the other. If one foot/leg is slower than the other, a coach could recommend or assign strength training and more attention on training drills to even the performance of both an athlete's feet or legs.

The ladder/hurdle drill of method 300 is described with reference to an athlete's performance over a generally flat surface. In another implementation, the data collection of method 300 may be applied to a step drill in which an athlete steps up to and down from one or more raised steps or platforms, such as a SPARQ Carlisle Speed BOX™ step drill platform available from SPARQ Marketing & Media of Portland, Oreg. The collection of acceleration data may be directed to counting step repetitions within fixed time and determining a foot contact time, as described above.

For example, step drill goals may include maximizing the number of foot strikes on the box or platform within a given time interval. In a drill version referred to as Step-Ups, the athlete steps quickly onto the box or platform with one foot and then, as soon as that foot lands on the box or platform, the other foot follows. The athlete then steps down in the same manner as quickly as possible. The goal is to minimize the number of steps in a given time interval such as by attempting to reduce the number of steps in subsequent drill sets. In addition to the number of foot strikes or steps, the amount of contact time can also be calculated and used in the manner described above. This can also be used for calculating athleticism ratings, improving athlete skills within the drill and as competition among various athletes.

As another example, multi-mode acceleration-based athleticism measurement system 100 can also be used in drills or tests that characterize stride length over a given distance, such as in sprints over a fixed distance (e.g., 40 yards).

Figure 4:
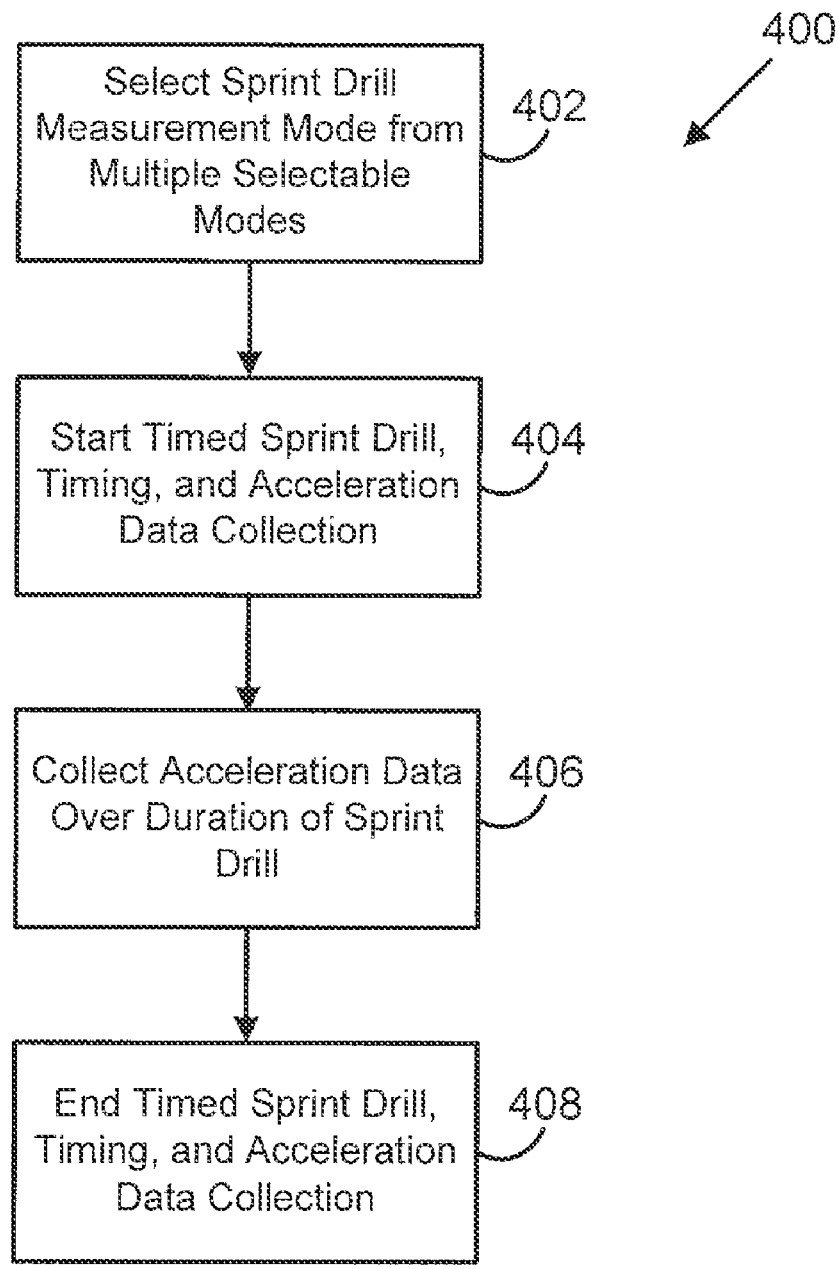
FIG. 4 is a flow diagram of a stride athletic performance measurement method as an illustration of another athleticism measurement mode according to the present invention.

FIG. 4 is a flow diagram of a stride athletic performance measurement method 400 that is performed during a fixed-distance sprint drill and may be used in connection with calculating an athletic performance rating or improving performance during sprint drills. In a fixed-distance sprint drill, an athlete runs as quickly as possible over the fixed distance. Conventionally, performance in a sprint drill is measured by measuring the overall time required for an athlete to run the fixed distance. The fixed-distance sprint athletic performance measurement may employ an acceleration sensor 102 positioned in or secured to one or each of the athlete's shoes, preferably an acceleration sensor 102 being positioned in or secured to each of the athlete's shoes.

In step 402 a sprint drill is selected from among multiple selectable drills or exercises, which correspond to different measurement modes, listed on athleticism rating processing device 106 that is worn or carried by the athlete.

In step 404 a timed sprint drill is started together with a start of timing of the overall drill duration and a start of collecting of acceleration data by athleticism measurement system 100 in a sprint drill mode. The acceleration data may be collected by athleticism rating processing device 106 that is worn or carried by the athlete. The start of timing of the overall drill duration may be initiated manually by an observer activating a timer or by the athlete crossing an optical timing start beam, and the start of collecting of acceleration data may be initiated by transmission of a wireless control signal to athleticism rating processing device 106 upon initiation of the overall timing.

In step 406 acceleration data are collected by athleticism measurement system 100 over the duration of the sprint drill.

In step 408 the timed sprint drill is ended together with timing of the overall drill duration and the collecting of acceleration data by athleticism measurement system 100. The timing of the overall drill duration may be ended manually by an observer de-activating a timer or by the athlete crossing an optical timing end beam, and the collecting of acceleration data may be ended by transmission of a wireless control signal to athleticism rating processing device 106 upon ending of the overall timing.

With an acceleration sensor 102 being positioned in or secured to each of the athlete's shoes, this acceleration data measurement mode can indicate the number of steps or strides over the fixed distance of the sprint drill. A drilling and testing goal of the sprint drill is for an athlete to minimize the number of steps or strides over the fixed-distance. The acceleration data, as an indicator of the number of steps or strides during a sprint drill, can be applied as a factor in using sprint drill results in an athleticism rating or as a guide to assist an athlete in improving sprint drill skills. For instance, a 40 yard sprint performed in 5.0 seconds with 20 strides may be performed in about 4.8 seconds with a lengthened stride that covers the distance in 19 strides. Moreover, acceleration data from both an athlete's shoes can identify asymmetry in the stride of an athlete's right and left legs. This asymmetry data can be applied as a factor in using sprint drill results in an athleticism rating or as a guide to assist an athlete in improving sprint drill skills.

It will be appreciated that in addition to determining stride length, as a number of strides over a fixed distance, the acceleration data in measurement method 400 can also indicate stride frequency and foot contact time. Moreover, the athlete may be given real-time feedback (e.g., audible) by athleticism rating processing device 106 during such a sprint drill. The feedback may indicate whether the athlete's performance meets or fails to meet a threshold stride frequency corresponding to a desired number of strides, or may cue the athlete with a cadence to a stride frequency. For example, in a 40 yard dash drill, audible feedback in the form of beeps or tones could initially have a relatively high frequency indicating quick acceleration strides and subsequently have al lower frequency corresponding to a longer, post-acceleration stride. At the end of the test or training drill, the athlete could review when the timing of his or her strides matched with the cued cadence and when it did not. Such cadence matching could be in addition to counting the total number of foot strikes and strides. Such data collection and feedback could be applied to other drills such as, for example, shuttle drills.

The measurement modes of agility athletic performance measurement method 300 and stride athletic performance measurement method 400 utilize each acceleration sensor 102 to measure acceleration generally along a vertical axis to detect foot strikes and associated performance characteristics. In another implementation, each acceleration sensor may measure acceleration along a lateral, generally horizontal axis to detect lateral changes in foot motion for measuring performance characteristics associated with an athlete changing direction from side-to-side. For example, such a vertical-lateral two-dimensional acceleration sensor 102 could be employed in athletic performance measurement method 300 to determine when an athlete changes direction relative foot placement to further characterize, or guide improvement in, performance of the drill. Also, the acceleration data in a lateral plan can be used to determine an agility or quickness rating. The two-dimensional acceleration data can be integrated over time to obtain velocity and a velocity vector to determine speed in linear and lateral dynamic movement, which can be applied in an athleticism rating of the athlete or guide the athlete toward improved performance in the particular drill.

As another example, multi-mode acceleration-based athleticism measurement system 100 with a vertical-lateral two-dimensional acceleration sensor 102 can be used in drills or tests that characterize direction-change reaction time in response to audible stimuli or commands.

Figure 5:
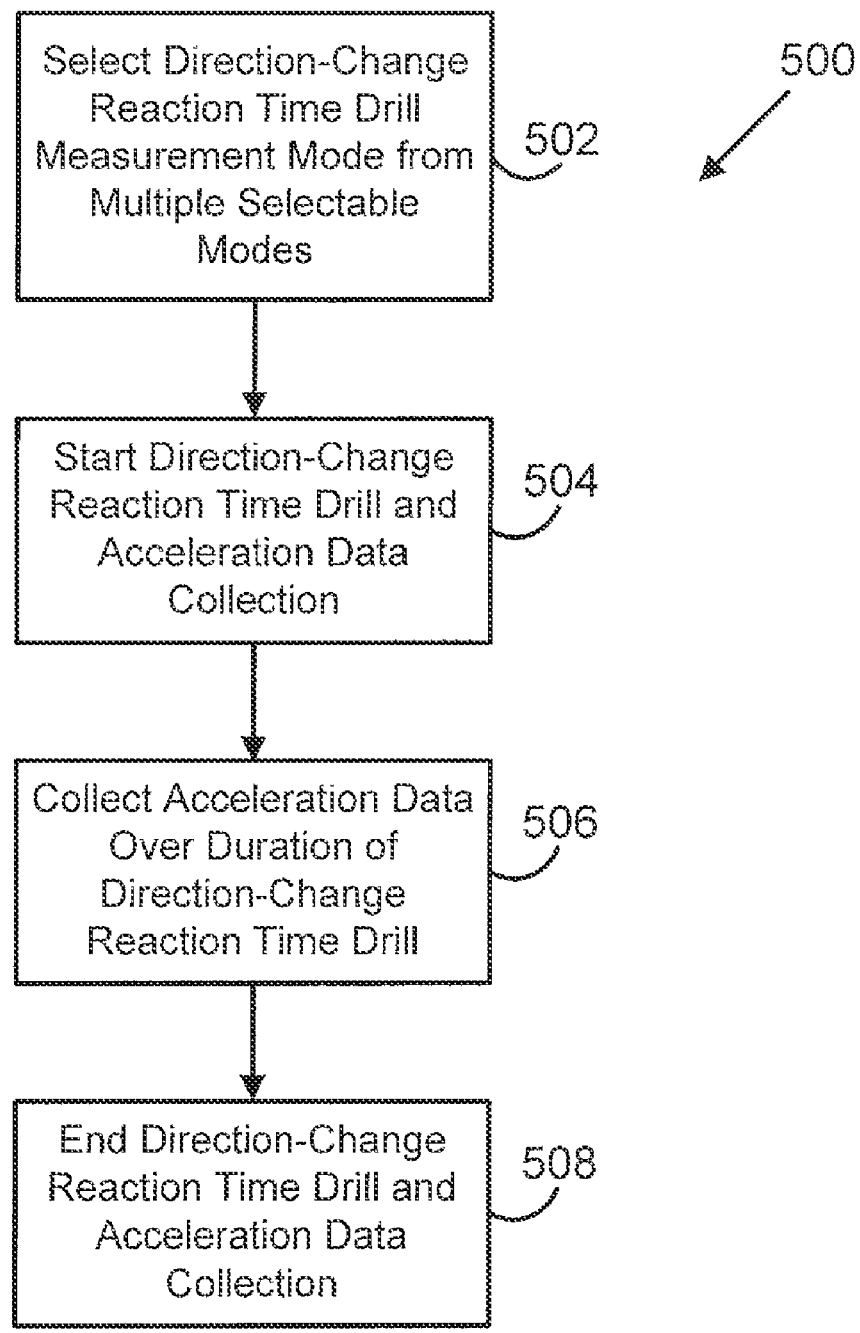
FIG. 5 is a flow diagram of a direction-change reaction time athletic performance measurement method as an illustration of yet another athleticism measurement mode according to the present invention.

FIG. 5 is a flow diagram of a direction-change reaction time athletic performance measurement method 500 that is performed as a direction-change reaction time drill over a selected number of samples and may be used in connection with calculating an athletic performance rating or improving performance during such reaction time drills. In a direction-change reaction time drill, an athlete changes lateral direction as quickly as possible in responses to triggers or commands, which may be provided audibly or visible. The following description is made with reference to audible triggers, but is similarly applicable to visible triggers. The direction-change reaction time athletic performance measurement may employ a vertical-lateral two-dimensional acceleration sensor 102 positioned in or secured to one or each of the athlete's shoes, preferably an acceleration sensor 102 being positioned in or secured to each of the athlete's shoes. Conventionally, direction-change reaction time drills are simply exercises and are not measured for lack of an available measurement device.

In step 502 a direction-change reaction time drill is selected from among multiple selectable drills or exercises, which correspond to different measurement modes, listed on athleticism rating processing device 106 that is worn or carried by the athlete.

In step 504 a direction-change reaction time drill is started together with a start of collecting of acceleration data by athleticism measurement system 100 in a direction-change reaction time drill mode. The acceleration data may be collected by athleticism rating processing device 106 that is worn or carried by the athlete. The start of collecting of acceleration data may be initiated by an audible cue generated by the athleticism rating processing device 106. In one implementation, the audible cue may be a simple tone or beep in response to which the athlete is to take a lateral step in a direction opposite of any prior lateral step. In another implementation, the audible cue may be a verbal instruction to take a lateral step in a specified direction. Preferably, the start of collecting of acceleration data begins after an audible warning that the drill is about to begin.

In step 506 acceleration data are collected by athleticism measurement system 100 over the duration of the direction-change reaction time drill.

In step 508 the direction-change reaction time drill is ended by an audible termination cue together with ending of the collecting of acceleration data by athleticism measurement system 100 based on a selected number or sequence of audible cues.

With a vertical-lateral two-dimensional acceleration sensor 102 being positioned in or secured to each of the athlete's shoes, the acceleration data measurement mode indicates the time duration between each audible cue and the resulting lateral step of the athlete, thereby measuring a lateral change of direction reaction time in response to each audible cue. A drilling and testing goal of the direction-change reaction time drill is for an athlete to minimize reaction time in response to a cue or stimulus. The acceleration data, as an indicator of the reaction time during the drill, can be applied as a factor in an athleticism rating calculation or as a guide to assist an athlete in improving direction-change reaction time skills.

Direction-change reaction time athletic performance measurement method 500 is described with reference to a vertical-lateral two-dimensional acceleration sensor 102. It will be appreciated that in other implementations acceleration sensor 102 may sense acceleration along vertical and axial axes and be used in a direction-change reaction time athletic performance measurement directed to forward and backward changes of direction. Alternatively, acceleration sensor 102 may sense acceleration along vertical, lateral, and axial axes and be used in a direction-change reaction time athletic performance measurement directed to lateral changes of direction as well as forward and backward changes of direction.

As another example, multi-mode acceleration-based athleticism measurement system 100 with a two-dimensional acceleration sensor 102 secured to one or each of an athlete's wrists, in addition to an acceleration sensor secured to one or both of the athlete's shoes, can be used in drills or tests that characterize directions of arm movement during running relative to running stride information. For example, a two-dimensional acceleration sensor 102 on each wrist can be used to determine and measure arm movement to characterize or guide improvement in the arm movement.

The arms have two main functions when running—developing a source of power and counter-acting unwanted rotation produced by running. An athlete's arm speed can increase overall running speed when the arm speed and motion are executed properly. In one characterization, proper arm movement includes forward movement extending the hands higher than the shoulders and backward movement extending hands behind the hips, all while the elbows are bent at 90-degrees and the hands do not cross the body bilateral centerline. At the moment of each foot strike, the opposite-side arm should be in front and starting to move back behind the hips. The change in direction of the arm will correspond to a change in direction of acceleration on the wrist-borne acceleration sensor 102.

Athlete arm movement performance information from wrist-borne acceleration sensors 102 may be collected together with running stride information collected from shoe-mounted sensors 102. The arm movement data may be used to characterize or guide improvement of an athlete's performance, either during a drill directed solely to measuring arm movement or during a drill that measures arm movement as well as stride or other information, such as information about synchronization of arm movement with foot strikes and stride. Arm movement characterizations may be based upon on samples of athletes of different heights running at different speeds to correlate the measured hand movement to a preferred full-range arm motion to guide athletes away from undesired short, fast arm movements. Moreover, real-time feedback can be applied to arm movement range or arm movement synchronization during a performance drill.

It will be appreciated that the measurement modes described with reference to FIGS. 2-5 are examples of multiple measurement modes in which multi-mode acceleration-based athleticism measurement system 100 can be used. Examples measurement modes in which multi-mode acceleration-based athleticism measurement system 100 can be used include stride frequency (Hz), flight time (per stride of average over time), maximum acceleration, maximum velocity, etc. Based on sample gait data for different velocities, from walking to running to sprinting, a stride length can be concluded from the acceleration data. Once a stride length is calculated, distance can be calculated from the foot strikes indicated by peak-to-peak acceleration data. In addition, a running average of velocity and acceleration can be computed to determine maximum acceleration and velocity during a training test or drill.

As another example, athleticism measurement system 100 can be used to determine athlete power based upon "explosiveness" of a first step movement. In this mode, acceleration data obtained during a vertical jump drill can directly indicate an athlete's loft time, from which a vertical height of the jump can be directly calculated, together with the forcefulness or power based upon the athlete's weight.

As yet another example, once the velocity curve over time is calculated, an area under the curve or a differential of a velocity over time curve can be used to determine an athlete's power expenditure. An athlete's maximum power can be calculated with respect to a maximum velocity as an upper limit. Similarly, a true power rating of athletic work performed can be expressed in watts (W).

In view of the many possible embodiments to which the principles of this invention may be applied, it should be recognized that the detailed embodiments are illustrative only and should not be taken as limiting the scope of our invention. Rather, the invention includes all such embodiments as may come within the scope and spirit of the following claims and equivalents thereto.

What is claimed is:

1. A system comprising:
   an athleticism processing device configured to determine athleticism information, the athleticism information corresponding to any of a first athleticism mode corresponding to a first athletic test involving a first type of athletic movement and a second athleticism mode corresponding to a second athletic test involving a second type of athletic movement,
   wherein the athleticism processing device is further configured to:
   generate a first set of one or more cues corresponding to instructions for a user to perform the first type of athletic movement at a specified time during the first athletic test when the first athleticism mode is selected;
   generate a second set of one or more cues, different from the first set of one or more cues, corresponding to instructions for the user to perform the second type of athletic movement at a specified time during the second athletic test when the second athleticism mode is selected, wherein the first set of one or more cues and the second set of one or more cues include at least one of: an audible cue, a visual cue and a haptic cue;
   process data received from one or more athletic activity sensors to generate a first set of one or more performance metrics when the first athleticism mode is selected; and
   generate a second set of one or more performance metrics when the second athleticism mode is selected, wherein the first set of one or more performance metrics is different from the second set of one or more performance metrics.

2. The system of claim 1, wherein the athleticism processing device is further configured to communicate over a data link to one or more other devices, wherein the data link is a wireless data link.

3. The system of claim 1 in which the athleticism processing device includes a wireless athlete timing system.

4. The system of claim 1 in which the athleticism processing device is borne by the athlete.

5. The system of claim 4, wherein the athleticism processing device is a wrist-worn device.

6. The system of claim 5, wherein the athleticism processing device includes the one or more athletic activity sensors.

7. The system of claim 1 in which the athleticism rating processing device provides real-time feedback of athletic performance to the user during performance of the first athletic test or the second athletic test.

8. The system of claim 7, wherein the real-time feedback includes an indication of whether the user performance meets a predefined performance threshold.

9. The system of claim 7 in which the real-time feedback includes an indication of whether the athletic performance matches the first set of one or more cues when the first athleticism mode is selected, wherein the first set of one or more cues includes cadence cues.

10. The system of claim 1, wherein the athleticism processing device is further configured to generate an athleticism rating of athletic performance using the first and second sets of performance metrics, wherein the athleticism rating comprises a single athleticism value generated based on performances in the first and second athleticism modes.

11. A method comprising:
    receiving, by an athleticism processing device, a selection of an athleticism measurement mode from among a plurality of athleticism measurement modes available on the athleticism processing device, each of the plurality of athleticism measurement modes corresponding to a different athletic test comprising a different type of athletic movement;
    generating, by the athleticism processing device, a first set of one or more cues corresponding to instructions for a user to perform a first type of athletic movement at a specified time during a first athletic test when a first athleticism measurement mode is selected;
    generating, by the athleticism processing device, a second set of one or more cues, different from the first set of one or more cues, corresponding to instructions for a user to perform a second type of athletic movement at a specified time during a second athletic test when a second athleticism measurement mode is selected, wherein the first set of cues and the second set of one or more cues include at least one of: an audible cue, a visual cue and a haptic cue;
    generating, by the athleticism processing device, a first set of one or more performance metrics based on activity sensor data when the selected athleticism measurement mode is the first athleticism measurement mode; and
    generating, by the athleticism processing device, a second set of one or more performance metrics based on the activity sensor data when the selected athleticism measurement mode is the second athleticism measurement mode.

12. The method of claim 11 further comprising providing real-time feedback of athletic performance to a user during performance of one or more of the first athletic test and the second athletic test.

13. The method of claim 12 in which the real-time feedback includes an indication of whether the user's performance meets a predefined performance threshold.

14. The method of claim 13 in which the real-time feedback includes an indication of whether the user's performance matches the first set of one or more cues when the first athleticism measurement mode is selected, wherein the first set of one or more cues includes cadence cues.

15. The method of claim 13 further comprising incorporating the first and second sets of one or more performance metrics into an athleticism rating of athletic performance.

16. The method of claim 11, wherein the activity sensor data is received from an athletic activity sensor.

17. The method of claim 16, wherein the athletic activity sensor is included in the athleticism processing device.

18. A system comprising:
    one or more wrist-worn sensors configured to sense athletic activity performed by a user; and
    an athleticism processing device configured to determine athleticism information based upon athletic activity data received from the one or more wrist-worn sensors, the athleticism information corresponding to any of a first athleticism mode corresponding to a first athletic test involving a first type of athletic movement and a second athleticism mode corresponding to a second athletic test involving a second type of athletic movement, wherein the athleticism processing device is different from the one or more wrist-worn sensors, wherein the athleticism processing device is further configured to:
  generate a first set of one or more cues corresponding to instructions for the user to perform the first type of athletic movement at a specified time during the first athletic test when the first athleticism mode is selected;
  generate a second set of one or more cues, different from the first set of one or more cues, corresponding to instructions for the user to perform the second type of athletic movement at a specified time during the second athletic test when the second athleticism mode is selected, wherein the first set of one or more cues and the second set of one or more cues include at least one of: an audible cue, a visual cue and a haptic cue;
  process the athletic activity data to generate a first set of one or more performance metrics when the first athleticism mode is selected; and
  generate a second set of one or more performance metrics when the second athleticism mode is selected, wherein the first set of one or more performance metrics is different from the second set of one or more performance metrics.

* * * * *